United States Patent
Nelson

(10) Patent No.: US 11,015,228 B2
(45) Date of Patent: May 25, 2021

(54) **ASSAY FOR DETECTING *CHLAMYDIA TRACHOMATIS*, *NEISSERIA GONORRHOEAE*, *TRICHOMONAS VAGINALIS*, AND *MYCOPLASMA GENITALIUM***

(71) Applicant: Abbott Molecular Inc., Des Plaines, IL (US)

(72) Inventor: Kevin Nelson, Des Plaines, IL (US)

(73) Assignee: Abbott Molecular Inc., Des Plaines, IL (US)

( * ) Notice: Subject to any disclaimer, the term of this patent is extended or adjusted under 35 U.S.C. 154(b) by 231 days.

(21) Appl. No.: 16/237,077

(22) Filed: Dec. 31, 2018

(65) Prior Publication Data

US 2019/0211379 A1 Jul. 11, 2019

Related U.S. Application Data

(60) Provisional application No. 62/615,057, filed on Jan. 9, 2018.

(51) Int. Cl.
*C12Q 1/68* (2018.01)
*C12Q 1/689* (2018.01)
*C12Q 1/6893* (2018.01)

(52) U.S. Cl.
CPC ........... *C12Q 1/689* (2013.01); *C12Q 1/6893* (2013.01); *C12Q 2600/16* (2013.01); *C12Q 2600/166* (2013.01)

(58) Field of Classification Search
None
See application file for complete search history.

(56) References Cited

U.S. PATENT DOCUMENTS

| | | | |
|---|---|---|---|
| 5,677,124 A | 10/1997 | Dubois et al. | |
| 5,919,625 A | 7/1999 | Dubois et al. | |
| 5,939,262 A | 8/1999 | Pasloske et al. | |
| 2008/0299567 A1* | 12/2008 | Marshall | C12Q 1/689 435/6.15 |
| 2011/0183339 A1 | 7/2011 | Getman | |

FOREIGN PATENT DOCUMENTS

| | | | |
|---|---|---|---|
| KR | 20120103801 A | 9/2012 | |
| WO | WO 2007083147 A2 | 7/2007 | |
| WO | WO-2010062001 A1 * | 6/2010 | ............. C12Q 1/689 |

OTHER PUBLICATIONS

"Birth of the digital bacteria". New Scientist, 215 (2875): 19 (2012).
Alexander et al., "Role of Chlamydia trachomatis in perinatal infection." Rev Infect Dis. Jul.-Aug. 1983;5(4):713-9.
Anagrius et al., "Mycoplasma genitalium: prevalence, clinical significance, and transmission." Sex Transm Infect. Dec. 2005;81(6):458-62.
Anonymous: "Amplisens T. Vaginalis/N. Gonorrhoeae/C.trachmomatis-Multiprime-FRT PCR kit." PCR Kit Instruction Manual, Sep. 29, 2011, pp. 1-13.
Berger et al., "Etiology, manifestations and therapy of acute epididymitis: prospective study of 50 cases." J Urol. Jun. 1979; 121(6):750-4.
Bøvre K. Family VIII Neisseriaceae Prévot 1933; 119. In: Krieg NR, Holt JG, editors. Bergey's Manual of Systematic Bacteriology. Baltimore, MD: Williams and Wilkins; 1984:288-96.
Brunham et al., "Mucopurulent cervicitis—the ignored counterpart in women of urethritis in men." N Engl J Med. Jul. 5, 1984; 311(1):1-6.
Carlson et al., "Comparative genomic analysis of Chlamydia trachomatis oculotropic and genitotropic strains." Infect Immun. Oct. 2005;73(10):6407-18.
Carlton et al., "Draft genome sequence of the sexually transmitted pathogen Trichomonas vaginalis." Science. Jan. 12, 2007; 315(5809):207-12.
Cates et al., "Genital chlamydial infections: epidemiology and reproductive sequelae." Am J Obstet Gynecol. Jun. 1991;164(6 Pt 2):1771-81.
Centers for Disease Control and Prevention, Sexually Transmitted Diseases Treatment Guidelines, MMWR Recomm Rep., 64(3) (2015).
Eisenstein et al., "Disseminated gonococcal infection (DGI) and gonococcal arthritis (GCA): I. Bacteriology, epidemiology, host factors, pathogen factors, and pathology." Semin Arthritis Rheum. Feb. 1981;10(3):155-72.
Fraser et al., "The minimal gene complement of Mycoplasma genitalium." Science. Oct. 20, 1995; 270(5235):397-403.
Glass et al., "Essential genes of a minimal bacterium." Proc Natl Acad Sci U S A. Jan. 10, 2006;103(2):425-30.
Hale et al. Evaluation of the PACE 2 Neisseria gonorrhoeae assay by three public health laboratories. J Clin Microbiol 1993;31(2):451-3.
Hook EW, and Hansfield HH. Gonococcal infection in the adult. In: Holmes KK, Mardh PA, Sparling PF, Lemon SM, Stamm WE, Piot P, Wasserheit J, (ed.) Sexually Transmitted Diseases. 3rd Ed. New York, NY: McGraw-Hill Book Co. 1999:451-66.
Janda WM, Knapp JS. Neisseria and Morexella catarrhalis. n: Murray PR, Baron, EJ, Jorgensen JH, Pfaller MA, Yolken RH, (ed.) Manual of Clinical Microbiology. 8th Ed. Washington DC: Amer. Soc. for Microbiology, 2003; 585-608.
Jeffrey et al., "Genome sequencing of recent clinical Chlamydia trachomatis strains identifies loci associated with tissue tropism and regions of apparent recombination." Infect Immun. Jun. 2010; 78(6):2544-53.

(Continued)

*Primary Examiner* — Juliet C Switzer
(74) *Attorney, Agent, or Firm* — Casimir Jones, S.C.; Melissa E. Karabinis

(57) ABSTRACT

The invention is directed to methods, kits, and compositions, for amplifying and detecting *Chlamydia trachomatis* (CT), *Neisseria gonorrhoeae* (NG), *Trichomonas vaginalis* (TV), and *Mycoplasma genitalium* (MG) in a sample, which comprises a variety of combinations of forward oligonucleotide primers, reverse oligonucleotide primers, and oligonucleotide probes.

19 Claims, No Drawings
Specification includes a Sequence Listing.

(56) References Cited

OTHER PUBLICATIONS

Joseph et al., "Genome-wide recombination in Chlamydia trachomatis." Nat Genet. Mar. 28, 2012;44(4):364-6.
Kissinger et al., "Trichomoniasis and HIV interactions: a review." Sex Transm Infect. Sep. 2013; 89(6):426-33.
Kissinger, "Trichomonas vaginalis: a review of epidemiologic, clinical and treatment issues." BMC Infect Dis. Aug. 5, 2015; 15:307.
Kumar et al., "Monoclonal antibodies to Chlamydia trachomatis: antibody specificities and antigen characterization." J Immunol. Mar. 1982; 128(3):1083-9.
Lefevre et al., "Screening for Chlamydia and gonorrhea: U.S. Preventive Services Task Force recommendation statement." Ann Intern Med. Dec. 16, 2014;161(12):902-10.
Lis et al., "Mycoplasma genitalium infection and female reproductive tract disease: a meta-analysis." Clin Infect Dis. Aug. 1, 2015;61(3):418-26.
Lusk et al., "Mycoplasma genitalium is associated with cervicitis and HIV infection in an urban Australian STI clinic population." Sex Transm Infect. Mar. 2011; 87(2):107-9.
Lyss et al., "Chlamydia trachomatis among patients infected with and treated for Neisseria gonorrhoeae in sexually transmitted disease clinics in the United States." Ann Intern Med. Aug. 5, 2003;139(3):178-85.
Marri et al., "Genome sequencing reveals widespread virulence gene exchange among human Neisseria species." PLoS One. Jul. 28, 2010;5(7):e11835.
McKenchnie et al., "Simultaneous identification of 14 genital microorganisms in urine by use of a multiplex PCR-based reverse line blot assay." J Clin Microbiol. Jun. 2009;47(6):1871-7.
MMWR Sexually transmitted diseases treatment guidelines, Morb. Mortal Wkly. Rep. [serial online]; 51 (RR-06) (2002).
Pasloske et al., "Armored RNA technology for production of ribonuclease-resistant viral RNA controls and standards." J Clin Microbiol. Dec. 1998;36(12):3590-4.
Pederson et al., "Typing Chlamydia trachomatis: from egg yolk to nanotechnology." FEMS Immunol Med Microbial. Mar. 2009;55(2):120-30.
Sacase Biotechnologes: "Multiplex Real lime PCR kit for qualitative detection of Chlamydia trachomatis, Neiserria gonorrhoeae and Trichomonas vaginalis", T.vaginalis/N. gonorrhoeae/C.trachomatis Real-TM Handbook, Nov. 14, 2011, pp. 1-12.
Schachter et al., "Chlamydial infections." West J Med. Nov. 1990;153(5):523-34.
Seth-Smith et al., "Co-evolution of genomes and plasmids within Chlamydia trachomatis and the emergence in Sweden of a new variant strain." BMC Genomics. May 21, 2009;10:239.
Seth-Smith et al., "Whole-genome sequences of Chlamydia trachomatis directly from clinical samples without culture." Genome Res. May 2013; 23(5):855-66.
Somboonna et al., "Hypervirulent Chlamydia trachomatis clinical strain is a recombinant between lymphogranuloma venereum (L(2)) and D lineages." mBia. May 3, 2011; 2(3):e00045-11.
Sparling PF & Handsfield HH, Neisseria gonorrhoeae. In: Mandell GL, Bennett JE, Dolin R, editors. Mandell, Douglas, and Bennet's Principles and Practice of Infectious Diseases. 5th Ed. Philadelphia, PA: Churchill Livingstone, Inc. 2000:2242-58.
Stephens et al., "Genome sequence of an obligate intracellular pathogen of humans: Chlamydia trachomatis." Science. Oct. 23, 1998; 282(5389):754-9.
Thomson et al., "Chlamydia trachomatis: genome sequence analysis of lymphogranuloma venereum isolates." Genome Res. Jan. 2008;18(1):161-71.
Unemo et al., "The Swedish new variant of Chlamydia trachomatis: genome sequence, morphology, cell tropism and phenotypic characterization." Microbiology (Reading). May 2010;156(Pt 5):1394-1404.
Van Der Pol et al., "Trichomonas vaginalis infection and human immunodeficiency virus acquisition in African women." J Infect Dis. Feb. 15, 2008; 197(4):548-54.
Wang et al., "Immunotyping of Chlamydia trachomatis with monoclonal antibodies." J Infect Dis. Oct. 1985;152(4):791-800.
Wang et al., "Multiplex polymerase chain reaction-based reverse line blot hybridization assay to detect common genital pathogens." Int J STD AIDS. May 2010; 21(5):320-5.
Weinstock et al., "Sexually transmitted diseases among American youth: incidence and prevalence estimates, 2000." Perspect Sex Reprod Health. Jan.-Feb. 2004; 36(1):6-10.

* cited by examiner

```
                        SEQUENCE LISTING

<160> NUMBER OF SEQ ID NOS: 18

<210> SEQ ID NO 1
<211> LENGTH: 21
<212> TYPE: DNA
<213> ORGANISM: Artificial Sequence
<220> FEATURE:
<223> OTHER INFORMATION: Synthetic

<400> SEQUENCE: 1
tcggagacca atggcccgta a                                              21

<210> SEQ ID NO 2
<211> LENGTH: 27
<212> TYPE: DNA
<213> ORGANISM: Artificial Sequence
<220> FEATURE:
<223> OTHER INFORMATION: Synthetic

<400> SEQUENCE: 2
gtttcgtgtc taaaccaaac gactctt                                        27

<210> SEQ ID NO 3
<211> LENGTH: 27
<212> TYPE: DNA
<213> ORGANISM: Artificial Sequence
<220> FEATURE:
<223> OTHER INFORMATION: Synthetic

<400> SEQUENCE: 3
agccagggag ttaagctaaa cggcgag                                        27

<210> SEQ ID NO 4
<211> LENGTH: 25
<212> TYPE: DNA
<213> ORGANISM: Artificial Sequence
<220> FEATURE:
<223> OTHER INFORMATION: Synthetic

<400> SEQUENCE: 4
ccggtttttg ttcatccgcc atatt                                          25

<210> SEQ ID NO 5
<211> LENGTH: 22
<212> TYPE: DNA
<213> ORGANISM: Artificial Sequence
<220> FEATURE:
<223> OTHER INFORMATION: Synthetic

<400> SEQUENCE: 5
cggctcctta ttcggtttga cc                                             22
```

<210> SEQ ID NO 6
<211> LENGTH: 18
<212> TYPE: DNA
<213> ORGANISM: Artificial Sequence
<220> FEATURE:
<223> OTHER INFORMATION: Synthetic

<400> SEQUENCE: 6
acaccgcccg gaacccga        18

<210> SEQ ID NO 7
<211> LENGTH: 22
<212> TYPE: DNA
<213> ORGANISM: Artificial Sequence
<220> FEATURE:
<223> OTHER INFORMATION: Synthetic

<400> SEQUENCE: 7
ctttgccgaa gtccttcggt ta        22

<210> SEQ ID NO 8
<211> LENGTH: 20
<212> TYPE: DNA
<213> ORGANISM: Artificial Sequence
<220> FEATURE:
<223> OTHER INFORMATION: Synthetic

<400> SEQUENCE: 8
gagtagcgca ccctctcagg        20

<210> SEQ ID NO 9
<211> LENGTH: 23
<212> TYPE: DNA
<213> ORGANISM: Artificial Sequence
<220> FEATURE:
<223> OTHER INFORMATION: Synthetic

<400> SEQUENCE: 9
atgctctggg ctgcacgcgt gct        23

<210> SEQ ID NO 10
<211> LENGTH: 24
<212> TYPE: DNA
<213> ORGANISM: Artificial Sequence
<220> FEATURE:
<223> OTHER INFORMATION: Synthetic

<400> SEQUENCE: 10
agcaatctgg tagcttgcaa aagt        24

<210> SEQ ID NO 11
<211> LENGTH: 22
<212> TYPE: DNA
<213> ORGANISM: Artificial Sequence
<220> FEATURE:
<223> OTHER INFORMATION: Synthetic

<400> SEQUENCE: 11
ccctacaacc cctatcctca ga        22

<210> SEQ ID NO 12
<211> LENGTH: 30
<212> TYPE: DNA
<213> ORGANISM: Artificial Sequence
<220> FEATURE:
<223> OTHER INFORMATION: Synthetic

```
<400> SEQUENCE: 12
cgaatgtgat tccgtgtgta gtggcgagcg                                    30

<210> SEQ ID NO 13
<211> LENGTH: 28
<212> TYPE: DNA
<213> ORGANISM: Artificial Sequence
<220> FEATURE:
<223> OTHER INFORMATION: Synthetic

<400> SEQUENCE: 13
ctacagcaga gttggcagct tcactttc                                      28

<210> SEQ ID NO 14
<211> LENGTH: 22
<212> TYPE: DNA
<213> ORGANISM: Artificial Sequence
<220> FEATURE:
<223> OTHER INFORMATION: Synthetic

<400> SEQUENCE: 14
gtctggcctt tcagcaagtt tc                                            22

<210> SEQ ID NO 15
<211> LENGTH: 25
<212> TYPE: DNA
<213> ORGANISM: Artificial Sequence
<220> FEATURE:
<223> OTHER INFORMATION: Synthetic

<400> SEQUENCE: 15
aagctgacga gttcatgagg gcagg                                         25

<210> SEQ ID NO 16
<211> LENGTH: 22
<212> TYPE: DNA
<213> ORGANISM: Artificial Sequence
<220> FEATURE:
<223> OTHER INFORMATION: Synthetic

<400> SEQUENCE: 16
ggcaggttgg tatcaaggtt ac                                            22

<210> SEQ ID NO 17
<211> LENGTH: 22
<212> TYPE: DNA
<213> ORGANISM: Artificial Sequence
<220> FEATURE:
<223> OTHER INFORMATION: Synthetic

<400> SEQUENCE: 17
cctaagggtg ggaaaataga cc                                            22

<210> SEQ ID NO 18
<211> LENGTH: 28
<212> TYPE: DNA
<213> ORGANISM: Artificial Sequence
<220> FEATURE:
<223> OTHER INFORMATION: Synthetic

<400> SEQUENCE: 18
tttctgatag gcactgactc tctctgcc                                      28
```

US 11,015,228 B2

ASSAY FOR DETECTING CHLAMYDIA TRACHOMATIS, NEISSERIA GONORRHOEAE, TRICHOMONAS VAGINALIS, AND MYCOPLASMA GENITALIUM

CROSS-REFERENCE TO RELATED APPLICATIONS

This application claims the benefit of U.S. Provisional Patent Application No. 62/615,057, filed Jan. 9, 2018, which is incorporated by reference herein.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 3,590 Byte ASCII (Text) file named "36075US2ORD_ST25.txt," created on Dec. 31, 2018.

BACKGROUND OF THE INVENTION

*Chlamydia trachomatis, N. gonorrhoeae, T. vaginalis,* and *M. genitalium* are among the most common non-viral sexually transmitted infections (STIs). Individuals infected with any of these pathogens are often asymptomatic or present with similar symptoms. However, treatment regimens are distinct for each pathogen. Thus, accurate methods for diagnosing each pathogen are required to ensure selection of appropriate treatment regimens. Currently, clinicians who suspect an STI typically run one assay at a time to detect each possible STI pathogen. In this regard, CT and NG typically are tested for initially, and only when those results are negative or the patient does not respond to antibiotic treatment are tests for TV or MG performed. For asymptomatic cases, generally only CT and NG are evaluated as part of normal annual screening programs.

Nucleic acid tests (NATs) that detect each of *C. trachomatis, N. gonorrhoeae, T vaginalis,* and *M. genitalium,* or the combination of CT and NG have been developed (see, e.g., Schachter J., *West. J. Med.,* 153(5): 523-34 (1990); Centers for Disease Control and Prevention, Sexually Transmitted Diseases Treatment Guidelines, MMWR Recomm Rep., 64(3) (2015); and Abbott REALTIME™ CT/NG Assay (Abbott Molecular, Des Plaines, Ill.)). Nucleic acid tests are typically performed using PCR reagents provided in liquid format that require frozen storage and batch testing, and turnaround time for sample preparation and real-time PCR can exceed several hours for some tests. NAT also is prone to handling errors such as contamination, and nucleic acid levels can drop below the limit of detection when the initial peak of infection resolves, especially when testing pooled samples.

Thus, there remains a need for more sensitive detection methods and systems for simultaneously detecting multiple STI pathogens in a single assay, which are provided in a format that eliminates or reduces storage requirements and PCR reagent waste. The present disclosure provides such methods and systems.

BRIEF SUMMARY OF THE INVENTION

The present disclosure provides a set of oligonucleotide sequences for amplifying and detecting *Chlamydia trachomatis* (CT), *Neisseria gonorrhoeae* (NG), *Trichomonas vaginalis* (TV), and *Mycoplasma genitalium* (MG) nucleic acid sequences in a sample. The set comprises (a) a primer and probe set that amplifies and detects at least a portion of the *Chlamydia trachomatis* 23S rRNA comprising a forward primer oligonucleotide sequence comprising SEQ ID NO: 1, a reverse primer oligonucleotide sequence comprising SEQ ID NO: 2, and a first probe oligonucleotide sequence comprising SEQ ID NO: 3; (b) a primer and probe set that amplifies and detects at least a portion of the *Neisseria gonorrhoeae* opa gene comprising a forward primer oligonucleotide sequence comprising SEQ ID NO: 4, a reverse primer oligonucleotide sequence comprising SEQ ID NO: 5, and a second probe oligonucleotide sequence comprising SEQ ID NO: 6; (c) a primer and probe set that amplifies and detects at least a portion of the *Trichomonas vaginalis* 18S rRNA comprising a forward primer oligonucleotide sequence comprising SEQ ID NO: 7, a reverse primer oligonucleotide sequence comprising SEQ ID NO: 8, and a third probe oligonucleotide sequence comprising SEQ ID NO: 9; and (d) a primer and probe set that amplifies and detects at least a portion of the *Mycoplasma genitalium* 23S rRNA comprising a forward primer oligonucleotide sequence comprising SEQ ID NO: 10, a reverse primer oligonucleotide sequence comprising SEQ ID NO: 11, and a fourth probe oligonucleotide sequence comprising SEQ ID NO: 12, wherein each of the probe oligonucleotide sequences comprises a detectable label. Also provided is a method for detecting CT, NG, TV, and MG in a sample using the aforementioned set of oligonucleotides.

The present disclosure also provides a kit for detecting *Chlamydia trachomatis* (CT), *Neisseria gonorrhoeae* (NG), *Trichomonas vaginalis* (TV), and *Mycoplasma genitalium* (MG) in a sample. The kit comprises (a) a primer and probe set that amplifies and detects at least a portion of the *Chlamydia trachomatis* 23S rRNA comprising a forward primer oligonucleotide sequence comprising SEQ ID NO: 1, a reverse primer oligonucleotide sequence comprising SEQ ID NO: 2, and a first probe oligonucleotide sequence comprising SEQ ID NO: 3; (b) a primer and probe set that amplifies and detects at least a portion of the *Neisseria gonorrhoeae* opa gene comprising a forward primer oligonucleotide sequence comprising SEQ ID NO: 4, a reverse primer oligonucleotide sequence comprising SEQ ID NO: 5, and a second probe oligonucleotide sequence comprising SEQ ID NO: 6; (c) a primer and probe set that amplifies and detects at least a portion of the *Trichomonas vaginalis* 18S rRNA comprising a forward primer oligonucleotide sequence comprising SEQ ID NO: 7, a reverse primer oligonucleotide sequence comprising SEQ ID NO: 8, and a third probe oligonucleotide sequence comprising SEQ ID NO: 9; (d) a primer and probe set that amplifies and detects at least a portion of the *Mycoplasma genitalium* 23S rRNA comprising a forward primer oligonucleotide sequence comprising SEQ ID NO: 10, a reverse primer oligonucleotide sequence comprising SEQ ID NO: 11, and a fourth probe oligonucleotide sequence comprising SEQ ID NO: 12; (e) reagents for amplifying and detecting nucleic acid sequences; and (f) instructions for use, wherein each of the probe oligonucleotide sequences comprises a detectable label.

The present disclosure also provides a composition for detecting *Chlamydia trachomatis* (CT), *Neisseria gonorrhoeae* (NG), *Trichomonas vaginalis* (TV), and *Mycoplasma genitalium* (MG) in a sample. The composition comprises (a) a primer and probe set that amplifies and detects at least a portion of the *Chlamydia trachomatis* 23S rRNA comprising a forward primer oligonucleotide sequence comprising SEQ ID NO: 1, a reverse primer oligonucleotide sequence comprising SEQ ID NO: 2, and a first probe oligonucleotide sequence comprising SEQ ID NO: 3; (b) a primer and probe set that amplifies and detects at least a portion of the *Neisseria gonorrhoeae* opa gene comprising a forward primer oligonucleotide sequence comprising SEQ ID NO: 4, a reverse primer oligonucleotide sequence comprising SEQ ID NO: 5, and a second probe oligonucleotide sequence comprising SEQ ID NO: 6; (c) a primer and probe set that amplifies and detects at least a portion of the *Trichomonas vaginalis* 18S rRNA comprising a forward primer oligonucleotide sequence comprising SEQ ID NO: 7, a reverse primer oligonucleotide sequence comprising SEQ ID NO: 8, and a third probe oligonucleotide sequence comprising SEQ ID NO: 9; and (d) a primer and probe set that amplifies and detects at least a portion of the *Mycoplasma genitalium* 23S rRNA comprising a forward primer oligonucleotide sequence comprising SEQ ID NO: 10, a reverse primer oligonucleotide sequence comprising SEQ ID NO: 11, and a fourth probe oligonucleotide sequence comprising SEQ ID NO: 12; wherein each of the probe oligonucleotide sequences comprises a detectable label.

DETAILED DESCRIPTION OF THE INVENTION

The present disclosure provides a set of oligonucleotides for amplifying and detecting four non-viral sexually-transmitted pathogens in a sample: *C. trachomatis, N. gonorrhoeae, T vaginalis,* and *M. genitalium*. The term "oligonucleotide," as used herein, refers to a short nucleic acid sequence comprising from about 2 to about to about 100 nucleotides (e.g., about 5, 10, 15, 20, 25, 30, 35, 40, 45, 50, 55, 60, 65, 70, 75, 80, 85, 90, 95, 99, or 100 nucleotides, or a range defined by any of the foregoing values). The terms "nucleic acid" and "polynucleotide" as used herein refer to a polymeric form of nucleotides of any length, either ribonucleotides (RNA) or deoxyribonucleotides (DNA). These terms refer to the primary structure of the molecule, and thus include double- and single-stranded DNA, and double- and single-stranded RNA. The terms include, as equivalents, analogs of either RNA or DNA made from nucleotide analogs and modified polynucleotides such as, for example, methylated and/or capped polynucleotides. Nucleic acids are typically linked via phosphate bonds to form nucleic acid sequences or polynucleotides, though many other linkages are known in the art (e.g., phosphorothioates, boranophosphates, and the like).

Oligonucleotides can be single-stranded or double-stranded, or can contain portions of both double-stranded and single-stranded sequences. The oligonucleotide can be DNA, both genomic and complimentary DNA (cDNA), RNA, or a hybrid, where the nucleic acid can contain combinations of deoxyribo- and ribonucleotides, and combinations of bases including uracil, adenine, thymine, cytosine, guanine, inosine, xanthine hypoxanthine, isocytosine and isoguanine. Oligonucleotides can be obtained by chemical synthesis methods or by recombinant methods. A particular oligonucleotide sequence can encompass conservatively modified variants thereof (e.g., codon substitutions), alleles, orthologs, single nucleotide polymorphisms (SNPs), and complementary sequences as well as the sequence explicitly indicated.

Chlamydia trachomatis

*Chlamydia* are non-motile, Gram-negative, obligate intracellular parasites of eukaryotic cells, which form inclusions in the cytoplasm of the host cell. *Chlamydia trachomatis* (CT) is the causative agent of the sexually transmitted disease (STD) *chlamydia*. Chlamydial infections of the urogenital tract are associated with salpingitis, ectopic pregnancies, and tubal factor infertility in women as well as non-gonococcal urethritis and epididymitis in men (see, e.g., Schachter, J., supra, Cates et al., *Am. J. Obstet. Gynecol.*, (6 Pt 2): 1771-1781 (1991); and Berger et al., *J. Urol.,* 121(6): 750-754 (1979)). The female genital site most commonly affected by *Chlamydia* in women is the cervix, but the infection can be asymptomatic and, if untreated, may ascend to the uterus, fallopian tubes, and ovaries, causing pelvic inflammatory disease (PID) (Brunham et al., *N Eng. J. Med.,* 311(1): 1-6 (1984)). Neonates born of infected mothers can contract inclusion conjunctivitis, asopharyngeal infections, and pneumonia due to CT (Alexander, E. R. and H. R. Harrison, *Rev. Infect. Dis.,* 5(4): 713-719 (1983)). Patients infected with CT may be co-infected with *Neisseria gonorrhoeae* (NG), the causative agent of gonorrhea. Furthermore, patients with treatment indications for gonorrhea but not *chlamydia* often harbor CT (Lyss et al., *Ann. Intern. Med.,* 139(3): 178-185 (2003)). Chlamydial infections may not respond well to recommended regimens for treating NG. Therefore, unless chlamydial infection has been ruled out in patients treated for gonorrhea, dual therapy for gonococcal and chlamydial infections typically is recommended (MMWR Sexually transmitted diseases treatment guidelines, Morb. Mortal Wkly. Rep. [serial online]; 51 (RR-06) (2002)).

Neisseria gonorrhoeae

*Neisseria gonorrhoeae* (NG) is a Gram-negative, oxidase-positive diplococcus without flagellae and is the causative agent of gonorrhea. Gonorrhea is one of the most common STDs in the United States, with over 700,000 new infections of NG estimated to occur each year (Weinstock et al., *Perspect Sex Reprod Health,* 36(1): 6-10 (2004)). In men, gonococcal infection usually results in acute anterior urethritis accompanied by a purulent exudate (Hook E W, and Hansfield H H., Gonococcal infection in the adult, In: Holmes K K, Mardh P A, Sparling P F, Lemon S M, Stamm W E, Piot P, Wasserheit J (eds.), Sexually Transmitted Diseases, 3rd Ed. New York, N.Y.: McGraw-Hill Book Co., pp. 451-66 (1999); and Sparling P F, Handsfield H H, *Neisseria gonorrhoeae*. In: Mandell G L, Bennett J E, Dolin R (eds.), *Mandell, Douglas, and Bennet's Principles and Practice of Infectious Diseases,* 5th Ed. Philadelphia, Pa.: Churchill Livingstone, Inc., pp. 2242-58 (2000)). In women, the infection is most often found in the cervix, but the vagina and uterus also may be infected. The infection is frequently asymptomatic, especially in women. Without treatment, local complications of gonococcal infection can occur, including PID or acute salpingitis for women and epididymitis for men (Hook and Hansfield, supra; and Sparling et al., supra). Rarely, disseminated gonococcal infection (DGI) may occur in untreated patients (Eisenstein, B. I. and A. T. Masi, *Semin. Arthritis Rheum.,* 10(3): 155-172 (1981)).

Trichomonas vaginalis

*Trichomonas vaginalis* (TV) is an anaerobic, protozoan parasite and the causative agent of trichomoniasis. The U.S. Centers for Disease Control and Prevention (CDC) estimates that 3.7 million people are infected with TV, making it the most common curable sexually transmitted infection in the U.S. (Centers for Disease Control and Prevention. Sexually Transmitted Diseases Treatment Guidelines, 2015. MMWR Recomm Rep., 64(3) (2015)). In women, infection with TV can cause vaginitis, urethritis, and cervicitis and is associated with PID tubal infertility, preterm delivery, low birth weight, and premature rupture of membranes (Centers for Disease Control and Prevention. Sexually Transmitted Diseases Treatment Guidelines, MMWR Recomm Rep., 64(3) (2015); Kissinger, P., *BMC Infect. Dis.*, 15: 307 (2015)). Women with TV infection are more susceptible to being infected by HIV and are at a higher risk of transmitting HIV to sexual partners (Van Der Pol et al., *J. Infect. Dis.*, 197: 548-554 (2008); and Kissinger, P. and A. Adamski, *Sex Transm. Infect.*, 89: 426-433 (2013)). In men, TV infection can cause non-gonococcal urethritis (NGU), epididymitis, or prostatitis (Van Der Pol et al., supra, and Kissinger and Adamski, supra). Between 70-85% of patients infected with TV are asymptomatic. Because of the adverse events associated with infection, screening may be considered for asymptomatic patients at high risk for infection, including those with multiple sex partners, illicit drug use, or a history of STD infections. Microscopic evaluation of wet mounts and TV culture are often used to diagnose TV infection; however, nucleic acid amplification tests have become the preferred method of TV detection due to their superior sensitivity (Centers for Disease Control and Prevention. Sexually Transmitted Diseases Treatment Guidelines, MMWR Recomm Rep., 64(3) (2015)).

Mycoplasma genitalium

Mycoplasma genitalium (MG) is a small, sexually-transmitted bacterium that colonizes the urogenital tract of both men and women. It is recognized as a cause of male nongonococcal urethritis (NGU), being responsible for 15-20% of NGU and 20-25% of non-chlamydial NGU (Anagrius et al., *Sex Transm. Infect.*, 81(6): 458-62 (2005)). In women, MG infection is detected in 10-30% of cervicitis cases, with infection being more common in women with cervicitis than without (Centers for Disease Control and Prevention. Sexually Transmitted Diseases Treatment Guidelines, MMWR Recomm Rep., 64(3) (2015), Anagrius et al., supra, and Lusk et al., *Sex Transm. Infect.*, 87: 107-109 (2011)). Recent evidence also indicates an association between MG infection and PID, preterm birth, and infertility (Lis et al., *Clin. Infect. Disease,* 61(3): 418-426 (2015)). Identifying MG infections is often a challenge, as most cases are asymptomatic or cause symptoms that resemble other STIs. Treatment regimens that are effective against other STIs typically show lower efficacy for MG infections (Centers for Disease Control and Prevention. Sexually Transmitted Diseases Treatment Guidelines, MMWR Recomm Rep., 64(3) (2015)).

Primer and Probe Oligonucleotides

Oligonucleotides are used in a variety of applications in biotechnology, such as, for example, artificial gene synthesis, as polymerase chain reaction (PCR) primers, in DNA sequencing, and as molecular probes. In one embodiment, the oligonucleotides described herein may be used as primers for nucleic acid amplification or as probes for nucleic acid hybridization and detection. The terms "primer," "primer sequence," and "primer oligonucleotide," as used herein, refer to an oligonucleotide which is capable of acting as a point of initiation of synthesis of a primer extension product that is a complementary strand of nucleic acid (all types of DNA or RNA), when placed under suitable amplification conditions (e.g., buffer, salt, temperature and pH) in the presence of nucleotides and an agent for nucleic acid polymerization (e.g., a DNA-dependent or RNA-dependent polymerase). A primer can be single-stranded or double-stranded. If double-stranded, the primer may first be treated (e.g., denatured) to allow separation of its strands before being used to prepare extension products. Such a denaturation step is typically performed using heat, but may alternatively be carried out using alkali, followed by neutralization. The primers of the present disclosure can be of any suitable size, and desirably comprise, consist essentially of, or consist of about 15 to 50 nucleotides, about 20 to 40 nucleotides, or about 22 to 30 nucleotides. The primers of the present disclosure can contain additional nucleotides in addition to those described herein. For example, depending on the type of amplification process employed, primers can include, for example, a restriction endonuclease recognition site 5' to the target binding sequence (see, e.g., U.S. Pat. Nos. 5,270,184 and 5,455,166), or an RNA polymerase promoter linked to the target binding sequence of the primer. A "forward primer" is a primer that hybridizes (or anneals) to a target nucleic acid sequence (e.g., template strand) for amplification. A "reverse primer" is a primer that hybridizes (or anneals) to the complementary strand of the target sequence during amplification. A forward primer hybridizes with a target sequence 5' with respect to a reverse primer.

The terms "probe," "probe sequence," and "probe oligonucleotide," refer to an oligonucleotide that can selectively hybridize to at least a portion of a target sequence under appropriate amplification conditions (e.g., a portion of a target sequence that has been amplified). In general, a probe sequence is identified as being either "complementary" (i.e., complementary to the coding or sense strand (+)), or "reverse complementary" (i.e., complementary to the antisense strand (−)). A probe can be single-stranded or double-stranded. If double-stranded, a probe oligonucleotide sequence may comprise a first nucleic acid sequence comprising a detectable label and a second nucleic acid sequence comprising a quencher moiety, as described in U.S. Pat. No. 9,388,455. The probes of the present disclosure can be of any suitable size, and desirably comprise, consist essentially of, or consist of about 10-50 nucleotides, about 12-35 nucleotides, or about 14-25 nucleotides.

As used herein, the terms "set," "primer set," "probe set," and "primer and probe set," refer to two or more oligonucleotide primers which together are capable of priming the amplification of a target sequence or target nucleic acid of interest (e.g., a target sequence within CT, NG, TV, or MG) and/or at least one probe which can detect the target sequence or target nucleic acid. In certain embodiments, the term "primer set" refers to a pair of primers including a forward primer (or 5' (upstream) primer) that hybridizes with the 5'-end of the target sequence or target nucleic acid to be amplified and a reverse primer (or 3' (downstream) primer) that hybridizes with the complement of the target sequence or target nucleic acid to be amplified. Such primer sets or primer pairs are particularly useful in PCR amplification reactions.

The set of oligonucleotides described herein may be used to amplify and detect one or more target nucleic acid sequences from CT, NG, TV, and MG in a sample. The terms "target sequence" and "target nucleic acid" are used interchangeably herein and refer to a specific nucleic acid sequence, the presence or absence of which is to be detected by the disclosed method. In the context of the present disclosure, a target sequence preferably includes a nucleic acid sequence to which one or more primers will hybridize and from which amplification will initiate. The target sequence can also include a probe-hybridizing region with which a probe may form a stable hybrid under appropriate hybridization conditions. A target sequence may be single-stranded or double-stranded, and more than one target sequence may be amplified and detected. The primer and probe sequences described herein can target any suitable nucleic acid sequence, or combination of sequences, present in the genome of CT, NG, TV, and MG.

The genome of *C. trachomatis* comprises a chromosome of 1.0 Mb and a plasmid of 7.5 kb which have been found to be highly conserved between strains, with few insertions/deletions and no variably present genomic islands identified to date (Stephens et al., *Science*, 282: 754-759 (1998); Carlson et al., *Infect Immun.*, 73: 6407-6418 (2005); Thomson et al., *Genome Res.*, 18: 161-171 (2008); Seth-Smith et al., *BMC Genomics*, 10: 239 (2009); Jeffrey et al., *Infect. Immun.*, 78: 2544-2553 (2010); Unemo et al., *Microbiology*, 156: 1394-1404 (2010); Somboonna et al., *MBio*, 2: e00045-11 (2011); Harris et al., *Nat Genet.*, 44: 364-366 (2012); and Seth-Smith et al., *Genome Res.*; 23(5): 855-866 (2013)). *C. trachomatis* strains have traditionally been classified into serovars based on the major outer membrane protein (MOMP), which represents the major surface antigen (Stephens et al., *J. Immunol.*, 128: 1083-1089 (1982); and Wang et al., *J. Infect. Dis.*, 152: 791-800 (1985)). Currently, genotyping of the ompA gene, which encodes MOMP, is more commonly performed (Pedersen et al., *FEMS Immunol. Med. Microbiol.*, 55: 120-130 (2009)). OmpA genotypes A-C have been associated with trachoma (the leading cause of infectious blindness worldwide), genotypes D-K have been associated with urogenital infections, and genotypes L1-L3 have been associated with the disease lymphogranuloma venereum (LGV) (Seth-Smith et al., *Genome Res.*; 23(5): 855-866 (2013)).

The set of oligonucleotides described herein may comprise, consist essentially of, or consist of any number of primer and probe oligonucleotides so as to amplify and detect any suitable number of CT nucleic acid sequences. In one embodiment, the set of oligonucleotides described herein comprises, consists essentially of, or consists of two or more primers which amplify at least a portion of the 23S rRNA of the CT genome to produce a single CT amplicon, and at least one probe which hybridizes to the single CT amplicon. This oligonucleotide set differs from other CT assays (e.g., REALTIME™ CT/NG assay (Abbott Molecular, Des Plaines, Ill.), which target the CT cryptic plasmid DNA. Targeting ribosomal RNA improves CT analytical sensitivity since the number of ribosomal RNA copies far exceeds the number of cryptic plasmid copies per organism. In this regard, the CT primer and probe set is designed to target sequences of the 23S ribosomal RNA that are highly conserved amongst all CT serovars, but do not cross react with RNA originating from commensal and closely related bacterial species.

A "portion" of a nucleic acid sequence comprises at least ten nucleotides (e.g., about 10 to about 5000 nucleotides). Preferably, a "portion" of a nucleic acid sequence comprises 10 or more (e.g., 15 or more, 20 or more, 25 or more, 30 or more, 35 or more, 40 or more, 45 or more, 50 or more, or 100 or more) nucleotides, but less than 5,000 (e.g., 4900 or less, 4000 or less, 3000 or less, 2000 or less, 1000 or less, 800 or less, 500 or less, 300 or less, or 100 or less) nucleotides. As used herein, the term "amplicon" refers to a product of a natural or artificial amplification reaction.

*Neisseria gonorrhoeae* comprises a circular genome of about 2.2 Mb, which encodes approximately 2,000 genes (Marri et al., *PLoS ONE*, 5(7): e11835 (2010)). The core *Neisseria* genome—the set of genes present in all *Neisseria* species—consists of 896 genes, most of which exhibit housekeeping functions. The opacity (Opa) genes encode proteins which are responsible for the opaque colony phenotype caused by tight junctions between adjacent *Neisseria*, and are also responsible for tight adherence to host cells. The set of oligonucleotides described herein may comprise, consist essentially of, or consist of any number of primer and probe oligonucleotides so as to amplify and detect any suitable number of NG nucleic acid sequences. In one embodiment, the set of oligonucleotides described herein comprises, consists essentially of, or consists of two or more primers which amplify at least a portion of the NG opa gene to produce a single NG amplicon, and at least one probe which hybridizes to the single NG amplicon.

The genome of *Trichomonas vaginalis* is approximately 160 Mb, two-thirds of which is comprised of repeats and transposable elements (Carlton et al., *Science*, 315(5809): 207-212 (2007)). The TV genome contains about 60,000 protein-coding genes, which is one of the highest coding capacities among eukaryotes (Carlton et al., supra). Introns have been identified in 65 genes. Transfer RNAs (tRNAs) for all 20 amino acids have been identified in the TV genome, and approximately 250 ribosomal DNA (rDNA) units have been localized to one of the six *T. vaginalis* chromosomes. The set of oligonucleotides described herein may comprise, consist essentially of, or consist of any number of primer and probe oligonucleotides so as to amplify and detect any suitable number of TV nucleic acid sequences. In one embodiment, the set of oligonucleotides described herein comprises, consists essentially of, or consists of two or more primers which amplify at least a portion of the 18S rRNA of the TV genome to produce a single TV amplicon, and at least one probe which hybridizes to the single TV amplicon.

The genome of *Mycoplasma genitalium* consists of 525 genes (New Scientist, 215 (2875): 19 (2012)) in one circular DNA of 580,070 base pairs (Fraser et al., *Science*, 270 (5235): 397-403 (1995)), making it one of the smallest genomes for a self-replicating organism. As such, the MG genome is thought to be a close approximation to the minimal set of genes needed to sustain bacterial life. Approximately 382 of the 482 *M. genitalium* protein-coding genes have been identified as essential, and genes encoding proteins of unknown function constitute 28% of the essential protein-coding genes set (Glass et al., *Proc. Natl. Acad. Sci. USA*, 103(2): 425-430 (2006)). The set of oligonucleotides described herein may comprise, consist essentially of, or consist of any number of primer and probe oligonucleotides so as to amplify and detect any suitable number of MG nucleic acid sequences. In one embodiment, the set of oligonucleotides described herein comprises, consists essentially of, or consists of two or more primers which amplify at least a portion of the 23S rRNA of the MG genome to produce a single MG amplicon, and at least one probe which hybridizes to the single MG amplicon.

In one embodiment, the set of oligonucleotides described herein comprises, consists essentially of, or consists of (a) a primer and probe set that amplifies and detects at least a portion of the *Chlamydia trachomatis* 23S rRNA comprising a forward primer oligonucleotide sequence comprising SEQ ID NO: 1, a reverse primer oligonucleotide sequence comprising SEQ ID NO: 2, and a first probe oligonucleotide sequence comprising SEQ ID NO: 3; (b) a primer and probe set that amplifies and detects at least a portion of the *Neisseria gonorrhoeae* opa gene comprising a forward primer oligonucleotide sequence comprising SEQ ID NO: 4, a reverse primer oligonucleotide sequence comprising SEQ ID NO: 5, and a second probe oligonucleotide sequence comprising SEQ ID NO: 6; (c) a primer and probe set that amplifies and detects at least a portion of the *Trichomonas vaginalis* 18S rRNA comprising a forward primer oligonucleotide sequence comprising SEQ ID NO: 7, a reverse primer oligonucleotide sequence comprising SEQ ID NO: 8, and a third probe oligonucleotide sequence comprising SEQ ID NO: 9; and (d) a primer and probe set that amplifies and detects at least a portion of the *Mycoplasma genitalium* 23S rRNA comprising a forward primer oligonucleotide sequence comprising SEQ ID NO: 10, a reverse primer oligonucleotide sequence comprising SEQ ID NO: 11, and a fourth probe oligonucleotide sequence comprising SEQ ID NO: 12, wherein each of the probe oligonucleotide sequences comprises a detectable label. The foregoing set of oligonucleotides is also referred to as ALINITY™ m STI.

The set of oligonucleotides described herein allows for the simultaneous detection of four of the most common non-viral STI pathogens in single test on a single sample, in contrast to other commercially available STI nucleic acid tests which detect and quantify only one or two STI pathogens at a time. When combined with internal control and cellular control primer and probe sets, as described herein, the set of oligonucleotides allows for more accurate detection of CT, NG, TV, and MG in a single assay. In addition, the set of oligonucleotides and detection method described herein allows for sample-to-result analysis in less time than other STI detection systems known in the art.

Any one or combination of the oligonucleotides described herein may be modified in any suitable manner so as to stabilize or enhance the binding affinity (also referred to as "melting temperature" or "$T_m$") of a primer or probe oligonucleotide for its target. In this respect, an oligonucleotide sequence as described herein may comprise one or more modified oligonucleotide bases. For example, the oligonucleotide sequence may comprise one or more propyne-modified bases, wherein the oligonucleotide comprises an alkyne with the chemical formula $CH_3C\equiv CH$. The one or more propyne-modified bases may include, for example, 5-(1-propynyl)-2'-deoxy-Uridine (pdU) and/or 5-(1-propynyl)-2'-deoxyCytidine (pdC).

Any one of the oligonucleotide sequences described herein may comprise, consist essentially of, or consist of a complement of any of the sequences disclosed herein. The terms "complement" or "complementary sequence," as used herein, refer to a nucleic acid sequence that forms a stable duplex with an oligonucleotide described herein via Watson-Crick base pairing rules, and typically shares about 80%, about 81%, about 82%, about 83%, about 84%, about 85%, about 86%, about 87%, about 88%, about 89%, about 90%, about 91%, about 92%, about 93%, about 94% about 95%, about 96%, about 97%, about 98% or about 99% greater identity with the inventive oligonucleotide. Nucleic acid sequence identity can be determined using any suitable mathematical algorithm or computer software known in the art, such as, for example, CLUSTAL-W, T-Coffee, and ALIGN (for alignment of nucleic acid and amino acid sequences), BLAST programs (e.g., BLAST 2.1, BL2SEQ, and later versions thereof) and FASTA programs (e.g., FASTA3x, FASTM, and SSEARCH) (for sequence alignment and sequence similarity searches). Sequence alignment algorithms also are disclosed in, for example, Altschul et al., *J. Molecular Biol.*, 215(3): 403-410 (1990); Beigert et al., *Proc. Natl. Acad. Sci. USA,* 106(10): 3770-3775 (2009), Durbin et al., eds., *Biological Sequence Analysis: Probalistic Models of Proteins and Nucleic Acids*, Cambridge University Press, Cambridge, UK (2009); Soding, *Bioinformatics,* 21(7): 951-960 (2005); Altschul et al., *Nucleic Acids Res.*, 25(17): 3389-3402 (1997); and Gusfield, *Algorithms on Strings, Trees and Sequences*, Cambridge University Press, Cambridge UK (1997)).

The oligonucleotides described herein may be prepared using any suitable method, a variety of which are known in the art (see, for example, Sambrook et al., *Molecular Cloning. A Laboratory Manual,* 1989, 2. Supp. Ed., Cold Spring Harbour Laboratory Press: New York, N.Y.; M. A. Innis (Ed.), *PCR Protocols. A Guide to Methods and Applications*, Academic Press: New York, N.Y. (1990); P. Tijssen, *Hybridization with Nucleic Acid Probes—Laboratory Techniques in Biochemistry and Molecular Biology (Parts I and II)*, Elsevier Science (1993); M. A. Innis (Ed.), *PCR Strategies*, Academic Press: New York, N.Y. (1995); F. M. Ausubel (Ed.), *Short Protocols in Molecular Biology*, John Wiley & Sons: Secaucus, N.J. (2002); Narang et al., *Meth. Enzymol.,* 68: 90-98 (1979); Brown et al., *Meth. Enzymol.*, 68: 109-151 (1979); and Belousov et al., *Nucleic Acids Res.,* 25: 3440-3444 (1997)). Primer pairs also can be designed using a variety of tools, such as the Primer-BLAST tool provided by the National Center of Biotechnology Information (NCBI). Oligonucleotide synthesis may be performed on oligo synthesizers such as those commercially available from Perkin Elmer/Applied Biosystems, Inc. (Foster City, Calif.), DuPont (Wilmington, Del.), or Milligen (Bedford, Mass.). Alternatively, oligonucleotides can be custom made and obtained from a variety of commercial sources well-known in the art, including, for example, the Midland Certified Reagent Company (Midland, Tex.), Eurofins Scientific (Louisville, Ky.), BioSearch Technologies, Inc. (Novato, Calif.), and the like. Oligonucleotides may be purified using any suitable method known in the art, such as, for example, native acrylamide gel electrophoresis, anion-exchange HPLC (see, e.g., Pearson et al., *J. Chrom.,* 255: 137-149 (1983)), and reverse phase HPLC (see, e.g., McFarland et al., *Nucleic Acids Res.,* 7: 1067-1080 (1979)).

The sequence of the primers and probes can be verified using any suitable sequencing method known in the art, including, but not limited to, chemical degradation (see, e.g., Maxam et al., *Methods of Enzymology,* 65: 499-560 (1980)), matrix-assisted laser desorption ionization time-of-flight (MALDI-TOF) mass spectrometry (see, e.g., Pieles et al., *Nucleic Acids Res.,* 21: 3191-3196 (1993)), mass spectrometry following a combination of alkaline phosphatase and exonuclease digestions (Wu et al. *Anal. Biochem.,* 290: 347-352 (2001)), and the like.

The primer and probe oligonucleotides described herein desirably comprise a melting temperature ($T_M$) in the range 45° C. to 80° C. In accordance with the present disclosure, the oligonucleotides specifically hybridize to a target nucleic acid sequence without exhibiting significant hybridization to non-target (i.e., non-CT, non-NG, non-TV, or non-MG nucleic acids). In addition, the oligonucleotides are selected such that they hybridize to conserved regions in the CT, NG, TV, and MG genomes, thus minimizing mismatches with the target sequence. Furthermore, the oligonucleotides are selected such that they show the least likelihood of dimer formation and contain minimal sequence repeats. Such properties can be determined by methods known in the art, for example, using the computer modelling program OLIGO® Primer Analysis Software (distributed by National Biosciences, Inc., Plymouth, Minn.).

Detectable Label

Any one or more of the primer and probe oligonucleotide sequences described herein may comprise a detectable label, such that the primer and/or probe can be visualized following binding to another entity (e.g., an amplification product or amplicon). The term "detectable label," as used herein, refers to a moiety or compound that generates a signal which can be measured and whose intensity is related to (e.g., proportional to) the amount of entity bound thereto. Any suitable detectable label that can be conjugated or linked to an oligonucleotide in order to detect binding of the oligonucleotide to a target sequence can be used, many of which are known in the art. In one embodiment, the detectable label may be detected indirectly. Indirectly detectable labels are typically specific binding members used in conjunction with a "conjugate" that is attached or coupled to a directly detectable label. Coupling chemistries for synthesizing such conjugates are well-known in the art and are designed such that the specific binding property of the specific binding member and the detectable property of the label remain intact. As used herein, "specific binding member" and "conjugate" refer to the two members of a binding pair, i.e. two different molecules, where the specific binding member binds specifically to the polynucleotide of the present invention, and the "conjugate" specifically binds to the specific binding member. Binding between the two members of the pair is typically chemical or physical in nature. Examples of such binding pairs include, but are not limited to, antigens and antibodies, avidin/streptavidin and biotin, haptens and antibodies specific for haptens, complementary nucleotide sequences, enzyme cofactors/substrates and enzymes, and the like.

In another embodiment, the detectable label may be directly detected. Such directly detectable labels include, for example, radioisotopes, fluorophores, chemiluminophores, enzymes, colloidal particles, fluorescent microparticles, intercalating dyes (e.g., SYBR Green or ethidium bromide), and the like. In one embodiment, the detectable label may be a fluorophore, such as a fluorescein-family dye, polyhalofluorescein-family dye, hexachlorofluorescein-family dye, coumarin-family dye, rhodamine-family dye, cyanine-family dye, oxazine-family dye, thiazin-family dye, squaraine-family dye, chelated lanthanide-family dye, azo-family dye, triphenylmethane-family dye, or a BODIPY®-family dye. Examples of fluorophores include, but are not limited to, FAM™, HEX™, JOE™, NED™, PET®, ROX™, TAMRA™, TET™, TEXAS RED®, and VIC®. One skilled in the art will appreciate that directly detectable labels may require additional components, such as substrates, triggering reagents, light, and the like, to enable detection of the label. Methods for labeling oligonucleotides, such as probes, are well-known in the art and described in, e.g., L. J. Kricka, *Ann. Clin. Biochem.*, 39: 114-129 (2002); van Gijlswijk et al., *Expert Rev. Mol. Diagn.*, 1: 81-91 (2001); Joos et al., *J. Biotechnol.*, 35: 135-153 (1994); Smith et al., *Nucl. Acids Res.*, 13: 2399-2412 (1985); Connoly et al., *Nucl. Acids. Res.*, 13: 4485-4502 (1985); Broker et al., *Nucl. Acids Res.*, 5: 363-384 (1978); Bayer et al., *Methods of Biochem. Analysis*, 26: 1-45 (1980); Langer et al., *Proc. Natl. Acad. Sci. USA*, 78: 6633-6637 (1981); Richardson et al., *Nucl. Acids Res.*, 11: 6167-6184 (1983); Brigati et al., *Virol.*, 126: 32-50 (1983); Tchen et al., *Proc. Natl. Acad. Sci. USA*, 81: 3466-3470 (1984); Landegent et al., *Exp. Cell Res.*, 15: 61-72 (1984); A. H. Hopman et al., *Exp. Cell Res.*, 169: 357-368 (1987); and Temsamani et al., *Mol. Biotechnol.*, 5: 223-232 (1996).

In another embodiment, any one or more of the primer and probe oligonucleotide sequences described herein may also comprise a quencher moiety. When the detectable label (e.g., a fluorophore) and quencher moiety are held in close proximity, such as at the ends of a probe, the quencher moiety prevents detection of a signal (e.g., fluorescence) from the detectable label. When the two moieties are physically separated, such as after cleavage by a DNA polymerase, the signal becomes detectable. The quencher may be selected from any suitable quencher known in the art, such as, for example, BLACK HOLE QUENCHER® 1 (BHQ-1®), BLACK HOLE QUENCHER® 2 (BHQ-2®), IOWA BLACK® FQ, and IOWA BLACK® RQ. For example, an oligonucleotide probe may comprise a FAM fluorophore and a BHQ-1 quencher.

Each of the probe oligonucleotide sequences in the set of oligonucleotide sequences described herein desirably comprises a detectable label. Each of the probes may be labeled with the same detectable label or different detectable labels. When the probes comprise the same detectable label (e.g., FAM), the amplified portions of the CT 23S rRNA, the NG opa gene, the TV 18S rRNA, and the MG 23S rRNA are detected as a single signal during real-time PCR. When each probe comprises a different detectable label, the amplified portions of the CT 23S rRNA, the NG opa gene, the TV 18S rRNA, and the MG 23S rRNA are detected as four separate signals.

The selection of a particular labeling technique will depend on several factors, such as the ease and cost of the labeling method, spectral spacing between different detectable labels used, the quality of sample labeling desired, the effects of the detectable moiety on the hybridization reaction (e.g., on the rate and/or efficiency of the hybridization process), the nature of the amplification method used, the nature of the detection system, the nature and intensity of the signal generated by the detectable label, and the like.

Internal Controls

The set of oligonucleotides for detecting CT, NG, TV, and MG described herein may further comprise primer and probe oligonucleotide sequences for amplifying and detecting an internal control (IC) sequence. In one embodiment, the internal control sequences are added to each sample preparation reaction. The internal control is then processed through the entire sample preparation and amplification procedure along with the test samples and calibrators (if present), to demonstrate proper sample processing and assay validity. In one embodiment, the internal control sequences are added directly to the PCR reaction to test for RT-PCR inhibition and demonstrate assay validity. The internal control may be any suitable non-CT, non-NG, non-TV, or non-MG nucleic acid sequence (also referred to as "exogenous" sequences), and desirably comprises, consists essentially of, or consists of an armored RNA target sequence. The term "armored RNA," as used herein, refers to RNase-resistant RNA that is a complex of MS2 bacteriophage coat protein and RNA produced in *Escherichia coli* by the induction of an expression plasmid that encodes the coat protein and an RNA standard sequence (see, e.g., Pasloske et al., *J. Clin. Microbiol.*, 36(12): 3590-359 (1998); and U.S. Pat. Nos. 5,677,124, 5,919,625, and 5,939,262). In one embodiment, for example, the internal control may comprise an RNA sequence derived or obtained from the hydroxypyruvate reductase gene of the pumpkin plant, *Curcurbita pepo*. In this regard, the set of oligonucleotides described herein may further comprise an internal control forward primer oligonucleotide sequence comprising SEQ ID NO: 13, an internal control reverse primer oligonucleotide sequence comprising SEQ ID NO: 14, and an internal control probe oligonucleotide sequence comprising SEQ ID NO: 15.

The set of oligonucleotides for detecting CT, NG, TV, and MG described herein may further comprise primer and probe oligonucleotide sequences for amplifying and detecting a cellular control, which is used as a control for sample input and preparation. In this respect, the cellular control primer and probe set may amplify and detect any suitable human gene, such as, for example, a human housekeeping gene. In one embodiment, the cellular control primer and probe set amplifies and detects the human β-globin gene and comprises a cellular control forward primer oligonucleotide sequence comprising SEQ ID NO: 16, a cellular control reverse primer oligonucleotide sequence comprising SEQ ID NO: 17, and a cellular control probe oligonucleotide sequence comprising SEQ ID NO: 18 and a detectable label.

Both the internal control probe and the cellular control probe desirably comprise a detectable label, such as any of those described herein. In one embodiment, the internal control probe and the cellular control probe may be labeled with distinct fluorophores that are different from the probes used to detect CT, NG, TV, and MG, which allows for simultaneous detection and differentiation of internal control, cellular control, and amplified target sequences within the same reaction. The internal control and cellular control probes may also comprise a quencher moiety, such as any of those described herein.

Method for Amplifying and Detecting *Chlamydia trachomatis* (CT), *Neisseria gonorrhoeae* (NG), *Trichomonas vaginalis* (TV), and *Mycoplasma genitalium* (MG)

The present disclosure provides a method for detecting CT, NG, TV, and MG in a sample suspected of containing CT, NG, TV, and MG. The method comprises: (a) contacting a sample obtained from a human with the set of oligonucleotide sequences described herein and reagents for amplification and detection of nucleic acid sequences, (b) amplifying a portion of the CT 23S rRNA sequence, a portion of the NG opa gene, a portion of the TV 18S rRNA, and a portion of the MG 23S rRNA present in the sample, (c) hybridizing the first, second, third, and fourth oligonucleotide probes to the amplified portion of the CT 23S rRNA, the NG opa gene, the TV 18S rRNA, and the MG 23S rRNA, respectively, (d) detecting hybridization of the first, second, third, and fourth oligonucleotide probes to the amplified portion of the CT 23S rRNA, the NG opa gene, the TV 18S rRNA, and the MG 23S rRNA, respectively by assessing a signal from each of the detectable labels, whereby (i) the presence of the signals indicates hybridization of first, second, third, and fourth oligonucleotide probes to the amplified portion of the CT 23S rRNA, the NG opa gene, the TV 18S rRNA, and the MG 23S rRNA, respectively, and the presence of CT, NG, TV, and MG in the sample, and (ii) the absence of the signals indicates the absence of CT, NG, TV, and MG in the sample. Descriptions of the primer and probe oligonucleotides set forth herein with respect to the aforementioned set of oligonucleotides also are applicable to those same aspects of the method described herein. The method described herein may be performed to detect any one or combination of CT, NG, TV, and/or MG simultaneously or sequentially. For example, a sample may be analyzed for the presence of CT only, CT and NG, CT and TV, NG only, NG and TV, TV only, TV and MG, MG only, NG and MG, CT, NG, and TV, and CT, NG, TV, and MG, and so on. Analysis of only one or a subset of CT, NG, TV, and MG results in "masking" of unselected pathogens, which may be useful in low prevalence areas where the positive predictive value of a particular assay is low.

A sample, as defined herein, is "suspected" of containing CT, NG, TV, and MG if the sample is obtained from a subject, preferably a human, suspected of being infected with CT, NG, TV, and MG. A subject is suspected of being infected with CT, NG, TV, and MG if the subject has an increased risk for contracting a sexually transmitted infection or disease (STI or STD). Factors that may increase the risk of STIs include, for example, having unprotected sex, sexual activity with multiple partners, a history of STIs, rape, injection drug use, age (half of STIs occur in people between 15 and 24 years of age), male prescription drug use for erectile dysfunction, and transmission from mother to infant during pregnancy.

The sample can be any suitable sample obtained from any suitable subject, typically a mammal, such as a human. The sample may be obtained from any biological source, such as a cervical tissue or fluid, vaginal tissue or fluid, endocervical tissue or fluid, or anal swab or brush, or a physiological fluid including, but not limited to, urine, whole blood, serum, plasma, interstitial fluid, saliva, ocular lens fluid, cerebral spinal fluid, sweat, milk, ascites fluid, mucous, nasal fluid, sputum, synovial fluid, peritoneal fluid, vaginal fluid, menses, amniotic fluid, semen, and the like. The sample can be obtained from the subject using routine techniques known to those skilled in the art, and the sample may be used directly as obtained from the biological source or following a pretreatment to modify the character of the sample. Such pretreatment may include, for example, preparing plasma from blood, diluting viscous fluids, filtration, precipitation, dilution, distillation, mixing, concentration, inactivation of interfering components, the addition of reagents, lysing, etc.

After the sample is obtained from a subject, the sample may be contacted with the set of oligonucleotides as described herein to form a reaction mixture. The reaction mixture is then placed under amplification conditions. The primers hybridize to a portion of the CT 23S rRNA sequence, a portion of the NG opa gene, a portion of the TV 18S rRNA, and/or a portion of the MG 23S rRNA if present in the sample, and the portions of the CT 23S rRNA sequence the NG opa gene, the TV 18S rRNA, and/or the MG 23S rRNA present in the sample are amplified.

Amplifying a CT, NG, TV, and/or MG nucleic acid sequence in the sample can be performed using any suitable nucleic acid sequence amplification method known in the art, including but not limited to, polymerase chain reaction (PCR), reverse-transcriptase PCR (RT-PCR), real-time PCR, transcription-mediated amplification (TMA), rolling circle amplification, nucleic acid sequence based amplification (NASBA), strand displacement amplification (SDA), and ligase chain reaction (LCR).

In one embodiment, RT-PCR, such as, for example, real-time RT-PCR, is performed to amplify *Chlamydia trachomatis* ribosomal RNA sequences, *Neisseria gonorrhoeae* genomic DNA sequences, *Trichomonas vaginalis* ribosomal RNA sequences, *Mycoplasma genitalium* ribosomal RNA sequences, an exogenous internal control RNA sequence, and human genomic DNA sequences. "RT-PCR," as used herein, refers to the enzymatic reaction in which complementary DNA (cDNA) fragments are synthesized from a substrate RNA template. The reaction typically involves the use of a synthetic oligonucleotide primer, which is complementary to nucleotide sequences in the substrate RNA, and the use of a reverse transcriptase enzyme. The reaction consists of one cycle, in which the oligonucleotide primers, which are present in vast excess, hybridize to the substrate RNA to form double-stranded structures along complementary nucleotide sequences. The primer-substrate DNA:RNA complexes will then serve as initiation sites for a cDNA synthesis reaction catalyzed by reverse transcriptase, resulting in the synthesis of a cDNA strand complementary to the RNA strand. The RNA may be a messenger RNA (mRNA), transfer RNA (tRNA), genomic RNA (gRNA), ribosomal RNA (rRNA), or a small nuclear RNA (snRNA). Methods and reagents for RT-PCR well known in the art and commercially available from a variety of sources (see, e.g., Freeman et al., *Biotechniques*, 26(1): 112-122, 142-125 (1999); Joyce, C., *Methods Mol. Biol.*, 193: 83-92 (2002);

and O'Connell, J. (ed.), *RT-PCR Protocols,* 1st Ed., Springer-Verlag, New York, N.Y. (2010)). Reverse transcription can be performed using one-step or two-step techniques known in the art, such as, for example, by using reverse transcription kits available from Thermo Fisher Scientific (Waltham, Mass.) Qiagen (Hilden, Germany), and Promega Corp. (Madison, Wis.).

"Real-time PCR," as used herein, refers to a PCR method in which the accumulation of amplification product is measured as the reaction progresses, in real time, with product quantification after each cycle, in contrast to conventional PCR in which the amplified DNA product is detected in an end-point analysis. Real-time PCR also is known in the art at "quantitative PCR (qPCR)." Real-time detection of PCR products typically involves the use of non-specific fluorescent dyes that intercalate with any double-stranded DNA and sequence-specific fluorescently-labeled DNA probes. Real-time PCR techniques and systems are known in the art (see, e.g., Dorak, M. Tevfik, ed., *Real-time PCR*, Taylor & Francis (2007); and Fraga et al., "Real-time PCR," Current protocols essential laboratory techniques: 10-3 (2008)) and are commercially available from a variety of sources (e.g., m2000rt REALTIME™ PCR system (Abbott Molecular, Inc., Des Plaines, Ill.); CFX Real-Time PCR Detection Systems (Bio-Rad Laboratories, Inc., Hercules, Calif.); and TAQMAN™ Real-Time PCR System (ThermoFisher Scientific, Waltham, Mass.)), any of which can be employed in the methods described herein.

Following amplification of portions of the CT 23S rRNA sequence, the NG opa gene, the TV 18S rRNA, and/or the MG 23S rRNA, if present in the sample, the method described herein further comprises hybridizing the first, second, third, and fourth oligonucleotide probes described herein to the amplified portion of the CT 23S rRNA, the NG opa gene, the TV 18S rRNA, and the MG 23S rRNA, respectively. In one embodiment, a reaction mixture comprising a CT 23S rRNA amplicon, a NG opa gene amplicon, a TV 18S rRNA amplicon, and a MG 23S rRNA amplicon may be contacted with first, second, third, and fourth oligonucleotide probes, as described herein, respectively, that preferentially hybridize to a target nucleic acid sequence of the amplicon, or the complement thereof, under stringent hybridization and wash conditions, thereby forming hybrid duplexes that are stable for detection. "Hybridization," as used herein, refers to the formation of a duplex structure by two single-stranded nucleic acids due to complementary base pairing. Hybridization can occur between fully complementary nucleic acid strands or between "substantially complementary" nucleic acid strands that contain minor regions of mismatch. "Stringent hybridization conditions," as used herein, means conditions under which hybridization of fully complementary nucleic acid strands is strongly preferred. Under stringent hybridization conditions, a first nucleic acid sequence (for example, a primer) will hybridize to a second nucleic acid sequence (for example, a target sequence), such as in a complex mixture of nucleic acids. Stringent conditions are sequence-dependent and will be different in different circumstances. Stringent conditions can be selected to be about 5-10° C. lower than the thermal melting point ($T_m$) for the specific sequence at a defined ionic strength pH. The $T_m$ can be the temperature (under defined ionic strength, pH, and nucleic acid concentration) at which 50% of an oligonucleotide complementary to a target hybridizes to the target sequence at equilibrium (as the target sequences are present in excess, at $T_m$, 50% of the probes are occupied at equilibrium). Stringent conditions can be those in which the salt concentration is less than about 1.0 M sodium ion, such as about 0.01-1.0 M sodium ion concentration (or other salts) at pH 7.0 to 8.3 and the temperature is at least about 30° C. for short probes (e.g., about 10-50 nucleotides) and at least about 60° C. for long probes (e.g., greater than about 50 nucleotides). Stringent conditions can also be achieved with the addition of destabilizing agents such as formamide. For selective or specific hybridization, a positive signal can be at least 2 to 10 times background hybridization. Exemplary stringent hybridization conditions include the following: 50% formamide, 5×SSC, and 1% SDS, incubating at 42° C., or, 5×SSC, 1% SDS, incubating at 65° C., with wash in 0.2×SSC, and 0.1% SDS at 65° C. Any suitable method and conditions for hybridizing oligonucleotide probes to a target nucleic acid sequence known in the art can be used in the method disclosed herein.

Following hybridization of the first, second, third, and fourth oligonucleotide probes described herein to the amplified portion of the CT 23S rRNA, the NG opa gene, the TV 18S rRNA, and the MG 23S rRNA, respectively, the method comprises detecting hybridization of the probe oligonucleotide sequences to the portions the CT 23S rRNA, the NG opa gene, the TV 18S rRNA, and the MG 23S rRNA by assessing a signal from each of the detectable labels, whereby (i) the presence of the signals indicates hybridization of first, second, third, and fourth oligonucleotide probes to the amplified portion of the CT 23S rRNA, the NG opa gene, the TV 18S rRNA, and the MG 23S rRNA, respectively, and the presence of CT, NG, TV, and MG in the sample, and (ii) the absence of the signals indicates the absence of CT, NG, TV, and MG in the sample. Detection of signals from the probe oligonucleotide sequences may be performed using a variety of well-known methodologies, including, for example homogeneous or heterogeneous techniques.

Homogeneous detection methods involve detecting products of the amplification reaction as they are formed, namely, in a real time manner. As a result, amplification product/probe hybrids are formed and detected while the reaction mixture is under amplification conditions. Homogeneous detection methods include, but are not limited to, the use of FRET labels that are attached to the probes and that emit a signal in the presence of the target sequence, Molecular Beacons (See, Tyagi et al., *Nature Biotechnol.,* 14: 303-308 (1996); Tyagi et al., *Nature Biotechnol.,* 16: 49-53 (1998); Kostrikis et al., *Science,* 279: 1228-1229 (1998); Sokol et al., *Proc. Natl. Acad. Sci. USA,* 95: 11538-11543 (1998); Marras et al., *Genet. Anal.,* 14: 151-156 (1999); and U.S. Pat. Nos. 5,846,726, 5,925,517, 6,277,581 and 6,235,504), TAQMAN® assays (see, e.g., U.S. Pat. Nos. 5,210,015; 5,804,375; 5,487,792 and 6,214,979 and International Patent Application Publication WO 01/86001), and hybridization protection assays (HPA) which utilize probes labeled with acridinium ester (AE) (see, e.g., Weeks et al., *Clin. Chem.,* 29: 1474-1479 (1983); Berry et al., *Clin. Chem.,* 34: 2087-2090 (1988)).

Heterogeneous detection systems generally employ a capture agent to separate amplified sequences from other materials in the reaction mixture. Capture agents typically comprise a solid support material (e.g., microtiter wells, beads, chips, and the like) coated with one or more specific binding sequences. A binding sequence may be complementary to a tail sequence added to oligonucleotide probes of the invention. Alternatively, a binding sequence may be complementary to a sequence of a capture oligonucleotide, itself comprising a sequence complementary to a tail sequence of a probe. After separation of the amplification product/probe hybrids bound to the capture agents from the remaining reaction mixture, the amplification product/probe hybrids can be detected using any suitable detection method known in the art or described herein.

Kits and Compositions for Amplifying and Detecting *Chlamydia trachomatis* (CT), *Neisseria gonorrhoeae* (NG), *Trichomonas vaginalis* (TV), and *Mycoplasma genitalium* (MG)

The invention also provides a kit for amplifying and detecting CT, NG, TV, and/or MG in a sample. The kit comprises primer and probe sets that amplify and detect a portion of the *Chlamydia trachomatis* 23 S rRNA, a portion of the *Neisseria gonorrhoeae* opa gene, a portion of the *Trichomonas vaginalis* 18 S rRNA, and/or a portion of the *Mycoplasma genitalium* 23S rRNA, and reagents and instructions for amplifying and detecting CT, NG, TV, and/or MG. Descriptions of the primer oligonucleotides and probe oligonucleotides set forth herein with respect to the aforementioned methods also are applicable to those same aspects of the kits described herein. Examples of suitable reagents for inclusion in the kit (in addition to the oligonucleotide primers and probes described herein) include conventional reagents employed in nucleic acid amplification reactions, such as, for example, one or more enzymes having polymerase activity, enzyme cofactors (such as magnesium or nicotinamide adenine dinucleotide (NAD)), salts, buffers, deoxyribonucleotide, or ribonucleotide triphosphates (dNTPs/rNTPs; for example, deoxyadenosine triphosphate, deoxyguanosine triphosphate, deoxycytidine triphosphate, and deoxythymidine triphosphate) blocking agents, labeling agents, and the like. Many such reagents are described herein or otherwise known in the art and commercially available.

In one embodiment, the kit may comprise, consist essentially of, or consist of (a) a primer and probe set that amplifies and detects a portion of the *Chlamydia trachomatis* 23S rRNA comprising a forward primer oligonucleotide sequence comprising SEQ ID NO: 1, a reverse primer oligonucleotide sequence comprising SEQ ID NO: 2, and a first probe oligonucleotide sequence comprising SEQ ID NO: 3; (b) a primer and probe set that amplifies and detects a portion of the *Neisseria gonorrhoeae* opa gene comprising a forward primer oligonucleotide sequence comprising SEQ ID NO: 4, a reverse primer oligonucleotide sequence comprising SEQ ID NO: 5, and a second probe oligonucleotide sequence comprising SEQ ID NO: 6; (c) a primer and probe set that amplifies and detects a portion of the *Trichomonas vaginalis* 18S rRNA comprising a forward primer oligonucleotide sequence comprising SEQ ID NO: 7, a reverse primer oligonucleotide sequence comprising SEQ ID NO: 8, and a third probe oligonucleotide sequence comprising SEQ ID NO: 9; (d) a primer and probe set that amplifies and detects a portion of the *Mycoplasma genitalium* 23S rRNA comprising a forward primer oligonucleotide sequence comprising SEQ ID NO: 10, a reverse primer oligonucleotide sequence comprising SEQ ID NO: 11, and a fourth probe oligonucleotide sequence comprising SEQ ID NO: 12; (e) reagents for amplifying and detecting nucleic acid sequences; and (f) instructions for use, wherein each of the probe oligonucleotide sequences comprises a detectable label.

The kit may comprise instructions for using the amplification reagents and primer and probe oligonucleotides described herein, e.g., for processing the test sample, extracting nucleic acid molecules, and/or performing the test; and for interpreting the results obtained, as well as a notice in the form prescribed by a governmental agency. Such instructions optionally can be in printed form or on CD, DVD, or other format of recorded media.

The present disclosure also provides a composition for amplifying and detecting CT, NG, TV, and/or MG in a sample. The composition comprises, consists essentially of, or consists of (a) a primer and probe set that amplifies and detects a portion of the *Chlamydia trachomatis* 23S rRNA comprising a forward primer oligonucleotide sequence comprising SEQ ID NO: 1, a reverse primer oligonucleotide sequence comprising SEQ ID NO: 2, and a first probe oligonucleotide sequence comprising SEQ ID NO: 3; (b) a primer and probe set that amplifies and detects a portion of the *Neisseria gonorrhoeae* opa gene comprising a forward primer oligonucleotide sequence comprising SEQ ID NO: 4, a reverse primer oligonucleotide sequence comprising SEQ ID NO: 5, and a second probe oligonucleotide sequence comprising SEQ ID NO: 6; (c) a primer and probe set that amplifies and detects a portion of the *Trichomonas vaginalis* 18S rRNA comprising a forward primer oligonucleotide sequence comprising SEQ ID NO: 7, a reverse primer oligonucleotide sequence comprising SEQ ID NO: 8, and a third probe oligonucleotide sequence comprising SEQ ID NO: 9; and (d) a primer and probe set that amplifies and detects a portion of the *Mycoplasma genitalium* 23S rRNA comprising a forward primer oligonucleotide sequence comprising SEQ ID NO: 10, a reverse primer oligonucleotide sequence comprising SEQ ID NO: 11, and a fourth probe oligonucleotide sequence comprising SEQ ID NO: 12; wherein each of the probe oligonucleotide sequences comprises a detectable label. Descriptions of the primer oligonucleotides and probe oligonucleotides set forth herein with respect to the aforementioned method and kit also are applicable to those same aspects of the composition described herein. In some embodiments, the composition comprises a carrier, preferably a pharmaceutically (e.g., physiologically acceptable) carrier. Any suitable carrier can be used within the context of the invention, and such carriers are well known in the art. The composition can optionally be sterile or sterile with the exception of the oligonucleotides described herein.

The aforementioned kit and composition may further comprise a primer and probe set that amplifies and detects an exogenous internal control nucleic acid sequence (e.g., the *Cucurbita pepo* hydroxypyruvate reductase gene), and a primer and probe set that amplifies and detects a cellular control nucleic acid sequence (e.g., the human β-globin gene), as described herein. In this regard, the kit and/or composition may comprise an internal control forward primer oligonucleotide sequence comprising SEQ ID NO: 13, an internal control reverse primer oligonucleotide sequence comprising SEQ ID NO: 14, and an internal control probe oligonucleotide sequence comprising SEQ ID NO: 15 and a detectable label. In another embodiment, the kit and/or composition may comprise a cellular control forward primer oligonucleotide sequence comprising SEQ ID NO: 16, a cellular control reverse primer oligonucleotide sequence comprising SEQ ID NO: 17, and a cellular control probe oligonucleotide sequence comprising SEQ ID NO: 18 and a detectable label.

The kit and/or composition may be supplied in a solid (e.g., lyophilized) or liquid form. In one embodiment, the primer oligonucleotides, probe oligonucleotides, and other reagents are lyophilized (i.e., freeze dried). Many nucleic acid detection systems known in the art provide PCR reagents in liquid format that requires frozen storage and batch testing. Lyophilization of the various components of the kit and composition described herein, however, eliminates the need for frozen storage and allows the assay components to be delivered in unit-dose format such that users may run the exact number of assays required, thereby minimizing reagent waste. The various components of the kits and composition of the present invention may optionally be contained within different containers (e.g., vial, ampoule, test tube, flask, or bottle) for each individual component (e.g., primer oligonucleotides, probe oligonucleotides, or buffer). Each component will generally be suitable as aliquoted in its respective container or provided in a concentrated form. Other containers suitable for conducting certain steps of the amplification/detection assay may also be provided. The individual containers are preferably maintained in close confinement for commercial sale.

The following example further illustrates the invention but, of course, should not be construed as in any way limiting its scope.

Example

This example demonstrates a method for amplifying and detecting *Chlamydia trachomatis, Neisseria gonorrhoeae, Trichomonas vaginalis,* and *Mycoplasma genitalium* in a sample in accordance with the present disclosure.

An assay that utilizes real-time RT-PCR to amplify and detect *Chlamydia trachomatis, Neisseria gonorrhoeae, Trichomonas vaginalis,* and *Mycoplasma genitalium* genomic sequences extracted from human specimens has been developed by Abbott Molecular, Inc. (Des Plaines, Ill.) under the brand name ALINITY™ m STI. The ALINITY™ m STI assay utilizes real time RT-PCR to amplify and detect *Chlamydia trachomatis* ribosomal RNA sequences, *Neisseria gonorrhoeae* genomic DNA sequences, *Trichomonas vaginalis* ribosomal RNA sequences, *Mycoplasma genitalium* ribosomal RNA sequences, and human genomic DNA sequences that have been extracted from endocervical swab specimens, vaginal swab specimens, male and female urine specimens, and gynecological specimens preserved in PRESERVCYT® solution (Hologic, Inc., Marlborough, Mass.). Endocervical swab, vaginal swab, and urine specimens are collected with the ALINITY™ m multi-Collect Specimen Transport Kit. PRESERVCYT® specimens are transferred to a transport tube for processing on the ALINITY™ m system.

The steps of the ALINITY™ m STI assay consist of sample preparation, RT-PCR assembly, amplification/detection, and result calculation and reporting. All stages of the ALINITY™ m STI assay procedure are executed automatically by the ALINITY™ m system. No intermediate processing or transfer steps are performed by the user. The ALINITY™ m system is designed to be a random access analyzer that can perform the ALINITY™ m STI assay in parallel with other ALINITY™ m assays on the same instrument.

Nucleic acids from specimens are extracted automatically on-board the ALINITY™ m instrument using the ALINITY™ m DNA Sample Prep Kit, ALINITY™ m Lysis Solution, and ALINITY™ m Diluent Solution. The ALINITY™ m instrument employs magnetic microparticle technology to facilitate nucleic acid capture, wash, and elution. In particular, at the beginning of the sample preparation protocol, sample (specimen or control) and magnetic microparticles are pipetted by the instrument into a sample preparation cartridge well containing ALINITY™ m Lysis Solution and ethanol. The conditions of the lysis step facilitate lysis of cells, denaturation of proteins, and dissociation of the bacteriophage capsid from armored RNA (for RNA targets in controls). The lysis conditions also promote nucleic acid binding to the magnetic microparticles. At the conclusion of the lysis step, magnetic microparticles with bound sample nucleic acids are captured by a magnetic plunger sheathed with a disposable plastic sleeve. The magnetic microparticles are then successively transferred to wells within the sample preparation cartridge containing a series of wash solutions. After wash steps are complete, the magnetic microparticles are captured by the plunger magnet and transferred into an elution well within the sample preparation cartridge where the purified nucleic acid is eluted off the microparticles into ALINITY™ m DNA Elution Buffer.

The resulting purified nucleic acids are then combined with a liquid unit-dose activator reagent, lyophilized unit-dose ALINITY™ m STI amplification reagents, and ALINITY™ m Vapor Barrier Solution, and transferred by the instrument to an amplification/detection module for reverse transcription, PCR amplification, and real-time fluorescence detection.

Assay controls are tested at or above an established minimum frequency to help ensure that instrument and reagent performance remain satisfactory. During each control event, a negative control and a positive control are processed through sample preparation and RT-PCR procedures that are identical to those used for specimens. Assay controls are used to demonstrate proper sample processing and assay validity. The ALINITY™ m STI amplification reagents include primers and probes that amplify and detect the single copy human gene, β-globin. Amplification and detection of the β-globin gene demonstrates proper sample processing and adequate sample input. An armored RNA internal control containing a sequence from the hydroxypyruvate reductase gene of the pumpkin plant, *Cucurbita pepo*, is included in each PCR reaction. The β-globin control and internal control are both used to demonstrate assay validity.

The primer and probe oligonucleotide sequences for amplification and detection of CT, NG, TV, MG, and internal and cellular controls are set forth below in Table 1. For the qualitative detection of *C. trachomatis* (CT), the ALINITY™ m STI assay is designed to target a region of the 23S ribosomal RNA. This design differs from the Abbott REALTIME™ CT/NG assay, which targets the CT cryptic plasmid DNA. Targeting ribosomal RNA improves CT analytical sensitivity since the number of ribosomal RNA copies far exceeds the number of cryptic plasmid copies per organism. The CT primer/probe set is designed to target sequences of the 23 S ribosomal RNA that are highly conserved amongst all CT serovars but do not cross react with RNA originating from commensal and closely related bacterial species. For qualitative detection of *N. gonorrhoeae* (NG), the ALINITY™ m STI assay is designed to target the multicopy opa gene. For the qualitative detection of *T. vaginalis* (TV), the ALINITY™ m STI assay is designed to target a region of the 18S ribosomal RNA. For qualitative detection of *M. genitalium* (MG), the ALINITY™ m STI assay is designed to target a region of the 23S ribosomal RNA.

TABLE 1

Primer and Probe Sequences

| Name | Oligo | Sequence (5' to 3') | SEQ ID NO |
|---|---|---|---|
| CT Fwd | Forward primer | TCG GAG ACC AAT GGC CCG TAA | 1 |
| CT Rev | Reverse primer | GTT TCG TGT CTA AAC CAA ACG ACT CTT | 2 |
| CT Probe | Probe | F-AGC CAG GGA GTT AAG CTA AAC GGC GAG-Q | 3 |
| NG Fwd | Forward primer | CCG GTT TTT GTT CAT CCG CCA TAT T | 4 |
| NG Rev | Reverse primer | CGG CTC CTT ATT CGG TTT GAC C | 5 |
| NG Probe | Probe | F-ACACCGCCCGGAACCCGA-Q | 6 |
| TV Fwd | Forward primer | CTT TGC CGA AGT CCT TCG GTT A | 7 |
| TV Rev | Reverse primer | GAG TAG CGC ACC CTC TCA GG | 8 |
| TV Probe | Probe | F-ATGCTCTGGGCTGCACGCGTGCT-Q | 9 |
| MG Fwd | Forward primer | AGC AAT CTG GTA GCT TGC AAA AGT | 10 |
| MG Rev | Reverse primer | CCC TAC AAC CCC TAT CCT CAG A | 11 |
| MG Probe | Probe | F-CGAATGTGATTCCGTGTGTAGTGGC GAGCG-Q | 12 |
| IC Fwd | Forward primer | CTA CAG CAG AGT TGG CAG CTT CAC TTT C | 13 |
| IC Rev | Reverse primer | GTC TGG CCT TTC AGC AAG TTT C | 14 |
| IC Probe | Probe | F-AAG CTG ACG AGT TCA TG GGG CAG G-Q | 15 |
| BG Fwd | Forward primer | GGC AGG TTG GTA TCA AGG TTA C | 16 |
| BG Rev | Reverse primer | CCT AAG GGT GGG AAA ATA GAC C | 17 |
| BG Probe | Probe | F-TTT CTG ATA GGC ACT GAC TCT CTC TGC C-Q | 18 |

F = fluorophore
Q = quencher

The assay utilizes two multi-well plates for nucleic acid amplification. One plate (master mix plate) contains the above-mentioned oligonucleotide primers and probes, PCR buffer components, reverse transcriptase, DNA polymerase, dNTP mix, armored RNA internal control, and excipients and is lyophilized (see Table 2). The second plate (activator plate) contains MgCl$_2$ and any monovalent salts needed for the reaction (see Table 3) and is stored as a liquid.

TABLE 2

Master Mix Well Components

| Component | Concentration |
|---|---|
| Alinity CT 23s rRNA Forward Primer | 0.115 μM |
| Alinity CT 23s rRNA Reverse Primer | 0.253 μM |
| Alinity CT 23s rRNA Probe | 0.092 μM |
| Alinity NG1 DNA Forward Primer | 0.221 μM |

TABLE 2-continued

Master Mix Well Components

| Component | Concentration |
|---|---|
| Alinity NG DNA Reverse Primer | 0.221 μM |
| Alinity NG1 DNA Probe | 0.147 μM |
| Alinity TV Forward Primer | 0.294 μM |
| Alinity TV Reverse Primer | 0.294 μM |
| Alinity TV Probe | 0.098 μM |
| Alinity MG Forward Primer | 0.221 μM |
| Alinity MG Reverse Primer | 0.221 μM |
| Alinity MG Probe | 0.098 μM |
| IC Forward Primer 196 | 0.217 μM |
| IC Reverse Primer 310 | 0.217 μM |
| Alinity IC RNA Probe (Q670) | 0.074 μM |
| Alinity BG DNA Forward Primer | 0.161 μM |
| Alinity BG DNA Reverse Primer | 0.161 μM |
| Alinity BG DNA Probe | 0.074 μM |

TABLE 2-continued

Master Mix Well Components

| Component | Concentration |
|---|---|
| HIV/HCV IC aRNA | Target CN |
| dNTPs | 0.540 mM |
| Ficoll 400<sup>&</sup> | 2.05% (W/V) |
| Ficoll 70<sup>&</sup> | 2.05% (W/V) |
| Trehalose<sup>&</sup> | 2.05% (W/V) |
| Melezitose<sup>&</sup> | 0.68% (W/V) |
| Tris-HCl | 55.187 mM |
| Tween 20 | 0.01% |
| Fish Gelatin | 0.01% |
| KAPA 2G Polymerase | 0.072 units/uL |
| SuperScript III Reverse Transcriptase | 0.196 units/uL |
| MgCl$_2$ | 5.94 mM |
| Tetramethyl Ammonium Chloride (TMAC) | 104.03 mM |
| KCl | 37.77 mM |
| ProClin 950 | 0.03% |

&Indicates Mastermix Reagent excipient component

TABLE 3

Activator Well Components

| Component | Concentration |
|---|---|
| MgCl$_2$ | 5.94 mM |
| Tetramethyl Ammonium Chloride (TMAC) | 104.03 mM |
| KCl | 37.77 mM |
| ProClin 950 | 0.03% |

For each sample, sample eluate and a defined volume of liquid activator are automatically transferred to the lyophilized master mix well to form the PCR reaction. The complete PCR reaction is then transferred to a thermocycler for amplification and detection without requiring additional operator manipulations.

During the first step of RT-PCR on the Abbott ALINITY™ m system, target RNA is converted to cDNA by the activity of a reverse transcriptase enzyme. The CT, TV, MG, and IC reverse primers anneal to their respective RNA targets and are extended during a short incubation period at a temperature that is permissive to reverse transcription activity. At the conclusion of the reverse transcription step, the reaction temperature rises to a temperature that dissociates double-stranded cDNA/RNA products generated during the reverse transcriptase step (from CT, TV, MG, and IC) as well as double-stranded DNA targets (from NG and human). This melting step also facilitates inactivation of the reverse transcriptase enzyme as well as hot start activation of the DNA polymerase. As the reaction temperature is subsequently lowered, CT, TV, MG, and IC forward primers anneal to their respective cDNA strands and are extended by the DNA polymerase. At the same time, the forward and reverse primers of NG and BG anneal to their respective genomic DNA strands and are extended by the DNA polymerase. During successive rounds of thermal cycling, amplification products dissociate to single strands at high temperature, followed by primer annealing and extension as the temperature is lowered. Exponential amplification is achieved through repeated cycling between high and low temperatures. Amplification of all six assay targets (CT, NG, TV, MG, BG, and IC) takes place simultaneously in the same reaction. The RT-PCR cycling conditions used by the ALINITY™ m STI assay are set forth in Table 4.

TABLE 4

PCR Cycling Protocol

| Cycles | Parameter | Description |
|---|---|---|
| 1 | 52° C./8 min | Reverse Transcription |
| 1 | 95° C./1 min, 70° C./2 min, 95° C./2 min | Hot Start Inactivation, Melt |
| 1 | 96° C./6 sec, 63° C./24 sec | DNA Melt/Amplification and Fluorescence Reads |

During the primer annealing/extension step, a read step is performed to allow real-time fluorescent detection of amplification products as probes anneal to their respective targets. In the absence of target, fluorescence is quenched. In the presence of target, probe hybridization to complementary sequences separates the fluorophore and the quencher, allowing fluorescent emission and detection. The amplification cycle number (CN) at which the fluorescent signal surpasses threshold specifications is used to detect the presence of target nucleic acid. Samples with a CN earlier than a defined CN cutoff are reported as positive, while samples with no CN or a CN later than the cutoff are reported as negative.

When selecting the STI assay for a given sample on the ALINITY M™ system, users will be able to select one or more pathogens at the start of a run. If a user wants to evaluate only CT or only CT and NG, for example, the user can select only those pathogens and the results of the unselected pathogens will be masked. This can be useful in hiding the result of pathogens in low prevalence areas where the positive predictive value is low.

The PCR formulation and cycling conditions described above may be further modified to optimize the assay.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. The phrase "consisting essentially of" also is construed to be an open-ended phrase meant to include steps or materials which do not materially affect the basic and novel characteristics of a described product or method. The phrase "consisting of" is construed to be a closed phrase which excludes any element, step, or ingredient not explicitly specified in the specification or claims. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A set of oligonucleotide sequences for amplifying and detecting *Chlamydia trachomatis* (CT), *Neisseria gonorrhoeae* (NG), *Trichomonas vaginalis* (TV), and *Mycoplasma genitalium* (MG) nucleic acid sequences in a sample, which comprises:
   (a) a primer and probe set that amplifies and detects at least a portion of the *Chlamydia trachomatis* 23S rRNA comprising a forward primer oligonucleotide sequence comprising SEQ ID NO: 1, a reverse primer oligonucleotide sequence comprising SEQ ID NO: 2, and a first probe oligonucleotide sequence comprising SEQ ID NO: 3;
   (b) a primer and probe set that amplifies and detects at least a portion of the *Neisseria gonorrhoeae* opa gene comprising a forward primer oligonucleotide sequence comprising SEQ ID NO: 4, a reverse primer oligonucleotide sequence comprising SEQ ID NO: 5, and a second probe oligonucleotide sequence comprising SEQ ID NO: 6;
   (c) a primer and probe set that amplifies and detects at least a portion of the *Trichomonas vaginalis* 18S rRNA comprising a forward primer oligonucleotide sequence comprising SEQ ID NO: 7, a reverse primer oligonucleotide sequence comprising SEQ ID NO: 8, and a third probe oligonucleotide sequence comprising SEQ ID NO: 9; and
   (d) a primer and probe set that amplifies and detects at least a portion of the *Mycoplasma genitalium* 23S rRNA comprising a forward primer oligonucleotide sequence comprising SEQ ID NO: 10, a reverse primer oligonucleotide sequence comprising SEQ ID NO: 11, and a fourth probe oligonucleotide sequence comprising SEQ ID NO: 12, wherein each of the probe oligonucleotide sequences comprises a detectable label.

2. The set of claim 1, which further comprises an internal control primer and probe set.

3. The set of claim 2, wherein the internal control primer and probe set comprises:
   (e) an internal control forward primer oligonucleotide sequence comprising SEQ ID NO: 13,
   (f) an internal control reverse primer oligonucleotide sequence comprising SEQ ID NO: 14, and
   (g) an internal control probe oligonucleotide sequence comprising SEQ ID NO: 15 and a detectable label.

4. The set of claim 1, which further comprises a cellular control primer and probe set.

5. The set of claim 4, wherein the cellular control primer and probe set amplifies and detects the human β-globin gene.

6. The set of claim 4, wherein the cellular control primer and probe set comprises:
   (h) a cellular control forward primer oligonucleotide sequence comprising SEQ ID NO: 16,
   (i) a cellular control reverse primer oligonucleotide sequence comprising SEQ ID NO: 17, and
   (j) a cellular control probe oligonucleotide sequence comprising SEQ ID NO: 18 and a detectable label.

7. The set of claim 1, wherein the detectable label is a fluorophore.

8. The set of claim 1, wherein each of the probe oligonucleotides further comprises a quencher moiety.

9. A method for detecting *Chlamydia trachomatis* (CT), *Neisseria gonorrhoeae* (NG), *Trichomonas vaginalis* (TV), and *Mycoplasma genitalium* (MG) in a sample suspected of containing *Chlamydia trachomatis*, *Neisseria gonorrhoeae*, *Trichomonas vaginalis*, and *Mycoplasma genitalium*, which method comprises:
   (a) contacting a sample obtained from a human with the set of oligonucleotide sequences of claim 1 and reagents for amplification and detection of nucleic acid sequences, and
   (b) detecting hybridization of the first, second, third, and/or fourth oligonucleotide probes to an amplified portion of the CT 23S rRNA, the NG opa gene, the TV 18S rRNA, and/or the MG 23S rRNA by assessing a signal from each of the detectable labels, whereby
      (i) the presence of a signal from any of the detectable labels indicates the presence of CT, NG, TV, and/or MG in the sample, and
      (ii) the absence of a signal from any of the detectable labels indicates the absence of CT, NG, TV, and/or MG in the sample.

10. The method of claim 9, wherein the sample comprises endocervical tissue or fluid, vaginal tissue or fluid, urine, or cervical tissue or fluid.

11. A kit for detecting *Chlamydia trachomatis* (CT), *Neisseria gonorrhoeae* (NG), *Trichomonas vaginalis* (TV), and *Mycoplasma genitalium* (MG) in a sample comprising
   (a) a primer and probe set that amplifies and detects at least a portion of the *Chlamydia trachomatis* 23S rRNA comprising a forward primer oligonucleotide sequence comprising SEQ ID NO: 1, a reverse primer oligonucleotide sequence comprising SEQ ID NO: 2, and a first probe oligonucleotide sequence comprising SEQ ID NO: 3;
   (b) a primer and probe set that amplifies and detects at least a portion of the *Neisseria gonorrhoeae* opa gene comprising a forward primer oligonucleotide sequence comprising SEQ ID NO: 4, a reverse primer oligonucleotide sequence comprising SEQ ID NO: 5, and a second probe oligonucleotide sequence comprising SEQ ID NO: 6;
   (c) a primer and probe set that amplifies and detects at least a portion of the *Trichomonas vaginalis* 18S rRNA comprising a forward primer oligonucleotide sequence comprising SEQ ID NO: 7, a reverse primer oligonucleotide sequence comprising SEQ ID NO: 8, and a third probe oligonucleotide sequence comprising SEQ ID NO: 9;
   (d) a primer and probe set that amplifies and detects at least a portion of the *Mycoplasma genitalium* 23S rRNA comprising a forward primer oligonucleotide sequence comprising SEQ ID NO: 10, a reverse primer oligonucleotide sequence comprising SEQ ID NO: 11, and a fourth probe oligonucleotide sequence comprising SEQ ID NO: 12;
   (e) reagents for amplifying and detecting nucleic acid sequences; and
   (f) instructions for use,
   wherein each of the probe oligonucleotide sequences comprises a detectable label.

12. The kit of claim 11, which further comprises an internal control primer and probe set.

13. The kit of claim 12, wherein the internal control primer and probe set comprises:
   (e) an internal control forward primer oligonucleotide sequence comprising SEQ ID NO: 13,
   (f) an internal control reverse primer oligonucleotide sequence comprising SEQ ID NO: 14, and
   (g) an internal control probe oligonucleotide sequence comprising SEQ ID NO: 15 and a detectable label.

14. The kit of claim 11, which further comprises a cellular control primer and probe set.

15. The kit of claim 14, wherein the cellular control primer and probe set amplifies and detects the human β-globin gene.

16. The kit of claim 14, wherein the cellular control primer and probe set comprises:
- (h) a cellular control forward primer oligonucleotide sequence comprising SEQ ID NO: 16,
- (i) a cellular control reverse primer oligonucleotide sequence comprising SEQ ID NO: 17, and
- (j) a cellular control probe oligonucleotide sequence comprising SEQ ID NO: 18 and a detectable label.

17. The kit of claim 11, wherein the primers, probes, and reagents are lyophilized.

18. A composition for amplifying and detecting *Chlamydia trachomatis* (CT), *Neisseria gonorrhoeae* (NG), *Trichomonas vaginalis* (TV), and *Mycoplasma genitalium* (MG) in a sample, which comprises:
- (a) a primer and probe set that amplifies and detects at least a portion of the *Chlamydia trachomatis* 23S rRNA comprising a forward primer oligonucleotide sequence comprising SEQ ID NO: 1, a reverse primer oligonucleotide sequence comprising SEQ ID NO: 2, and a first probe oligonucleotide sequence comprising SEQ ID NO: 3;
- (b) a primer and probe set that amplifies and detects at least a portion of the *Neisseria gonorrhoeae* opa gene comprising a forward primer oligonucleotide sequence comprising SEQ ID NO: 4, a reverse primer oligonucleotide sequence comprising SEQ ID NO: 5, and a second probe oligonucleotide sequence comprising SEQ ID NO: 6;
- (c) a primer and probe set that amplifies and detects at least a portion of the *Trichomonas vaginalis* 18S rRNA comprising a forward primer oligonucleotide sequence comprising SEQ ID NO: 7, a reverse primer oligonucleotide sequence comprising SEQ ID NO: 8, and a third probe oligonucleotide sequence comprising SEQ ID NO: 9; and
- (d) a primer and probe set that amplifies and detects at least a portion of the *Mycoplasma genitalium* 23S rRNA comprising a forward primer oligonucleotide sequence comprising SEQ ID NO: 10, a reverse primer oligonucleotide sequence comprising SEQ ID NO: 11, and a fourth probe oligonucleotide sequence comprising SEQ ID NO: 12; wherein each of the probe oligonucleotide sequences comprises a detectable label.

19. The composition of claim 18, wherein the primer oligonucleotides, probe oligonucleotides, and reagents are lyophilized.

* * * * *